United States Patent [19]

Pfleger

[11] 4,334,536

[45] Jun. 15, 1982

[54] HYPODERMIC SYRINGE NEEDLE ASSEMBLY

[76] Inventor: Frederick W. Pfleger, 1152 Barbara Dr., Cherry Hill, N.J. 08003

[21] Appl. No.: 204,319

[22] Filed: Nov. 5, 1980

[51] Int. Cl.³ .............................................. A61M 5/00
[52] U.S. Cl. ................................................ 128/218 DA
[58] Field of Search ....... 128/218 DA, 218 N, 218 R, 128/215, 216, 220, 221

[56] References Cited

U.S. PATENT DOCUMENTS

| | | | |
|---|---|---|---|
| 3,828,775 | 8/1974 | Armel | 128/218 N |
| 3,930,499 | 1/1976 | Rimbaud | 128/218 DA |
| 3,989,044 | 11/1976 | Meierhoefer | 128/218 N |
| 4,009,716 | 3/1977 | Cohen | 128/218 DA X |

*Primary Examiner*—John D. Yasko

[57] ABSTRACT

A hypodermic syringe needle assembly for prefilled syringes in which the means for attaching the needle assembly to a syringe, the cover for the portion of the needle used for injecting and the cover for the portion of the needle used to activate the syringe is a unitized structure. This structure is breakable at a specific break point when the prefilled syringe is activated for use and breakable at another specific break point to expose the injection needle.

15 Claims, 4 Drawing Figures

U.S. Patent  Jun. 15, 1982  4,334,536
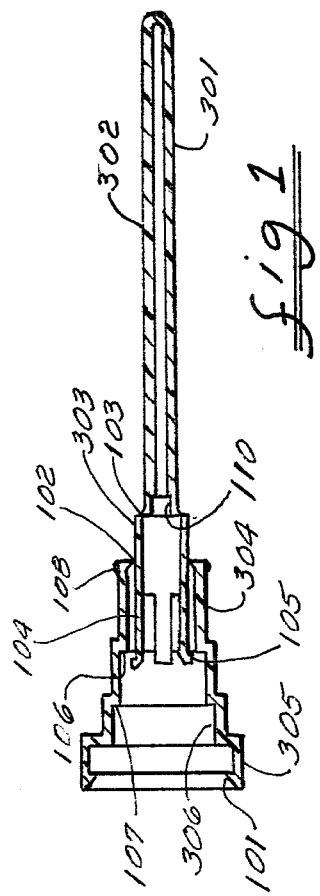
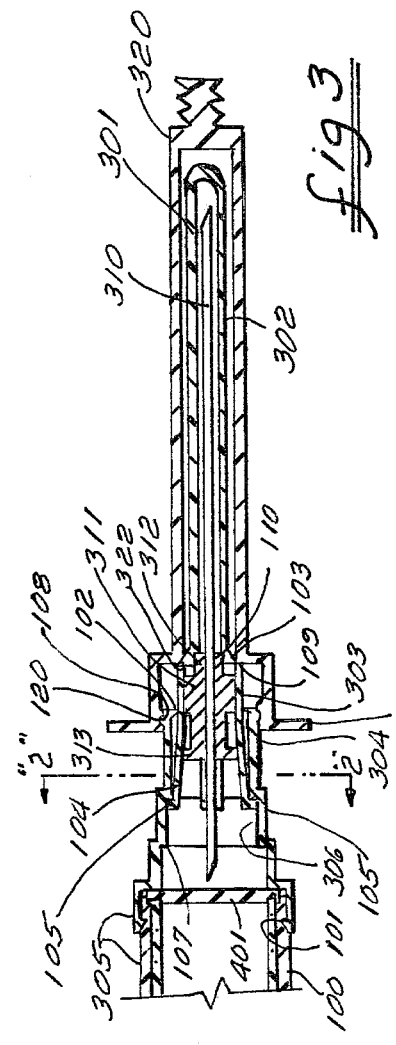
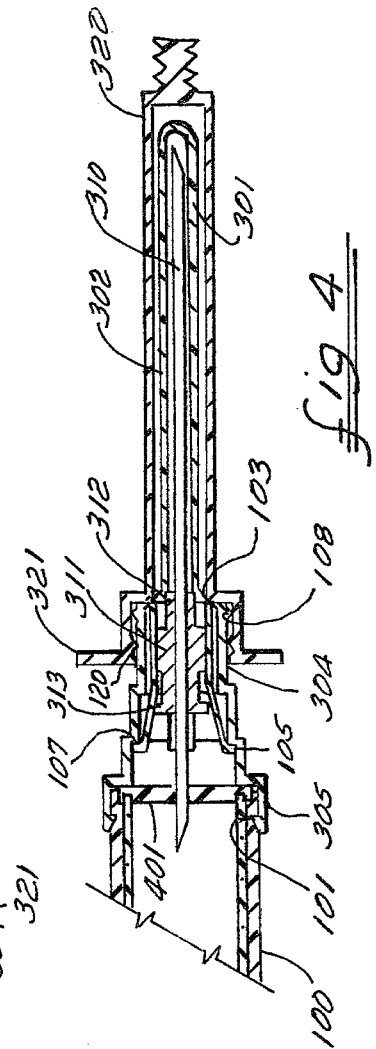
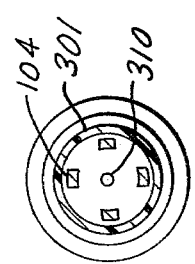

HYPODERMIC SYRINGE NEEDLE ASSEMBLY

BACKGROUND OF INVENTION

In disposable hypodermic syringe, U.S. Pat. No. 4,221,218, a syringe closing member, a needle holder and a cover were specifically described. These components are fabricated as individual pieces, assembled to each other to form an assembly and then fastened to the syringe body. All these manufacturing steps are expensive and are susceptible to rejects. The components described in the referenced patent provide for sterility to airborne contaminants because of the Pasteur principle of Tortuous Pathway. The syringe would not maintain sterility if submersed in water or other fluids. As a result, to reduce cost and make the needle assembly sterile under all conditions it is desirable that the needle assembly be made with as few parts as possible and that there be no voids or openings between any of the parts making up the needle assembly. Since the needle should be protected from damage in handling it is important that the needle assembly should also act as a mechanical protection for the needle. In most prefilled syringes the needle does not contact the fluids of the syringe when the syringe is in storage or shipment. To use the syringe one end of the needle pierces a seal between the needle and the fluid to allow transfer of the fluid through the needle to the person or animal being injected. The activation of the needle from the non-activated position with respect to the syringe to the activated position should be capable of being performed with the minimum amount of motion and the minimum amount of effort. Since the sterility of that portion of the needle that pierces the seal and the portion of the needle that is injected into a person or animal is very ctitical, the needle covers should never accidentally fall off or dislodge from the assembly and expose any part of the needle. In existing needle cover assemblies extremely close tolerances must be held between mating parts to assure that accidental separation does not take place and that excess forces are not required to operate the syringes. As a result the number of parts required, the assembly of the parts and the accuracy of the parts of syringe needle assemblies that are available today are costly and still do not provide all of the desired features of an ideal assembly.

SUMMARY OF INVENTION

It is therefore a first object of this invention to provide a hypodermic syringe needle assembly with as few parts and as few assembly operations as possible.

It is a further object of this invention to provide a hypodermic syringe needle assembly in which the components of the assembly insure normal sterility.

It is a further object of this invention to provide a hypodermic syringe needle assembly which is capable of maintaining sterility even if immersed in a fluid.

It is a further object of this invention to provide a hypodermic syringe needle assembly which makes activating of a prefilled syringe easy to accomplish.

It is a further object of this invention to provide a hypodermic syringe needle assembly which is reliable and can be provided at a minimum cost.

These and other objects of this invention will become apparent from the following specifications and drawings which form part of this disclosure. This invention therefore consists of unique features of construction, materials, and combinations which will provide a minimum cost and a highly reliable hypodermic syringe needle assembly, the scope of which is indicated by the appended claims.

DESCRIPTION OF DRAWINGS

FIG. 1 is a longitudinal sectional view through the needle cover before assembly with a needle.

FIG. 2 is a cross section along line 2—2 of FIG. 3.

FIG. 3 is a longitudinal cross section of the needle assembly with the needle assembled with the cover and the assembly attached to the syringe in the deactivated position.

FIG. 4 is a longitudinal section through the assembly with the needle assembled with the cover and the needle assembly in activated position with the syringe.

DESCRIPTION OF PREFERRED EMBODIMENT

Referring to FIG. 3, the needle assembly comprises a needle 310, a needle holder 311, and a needle cover 301. The outer portion 302 of needle cover 301 covers the outer portion of the needle 310, a middle portion 303 of needle cover 301 covers the needle holder 311 which is fastened to the middle portion of needle 310, and an inner portion 304 of needle cover 301 covers the inner portion of needle 310. The inner portion 304 is provided with an assembly flange 305 which attaches to the syringe body 100 and is secured by a groove 101 acting with assembly flange 305 of the needle assembly. The portions 302, 303, 304 and 305, as shown in FIG. 1, are fabricated in one piece such as by plastic molding. The portions are joined together by means of connecting webs 102 and 103. Since connecting web 102 extends completely around inner portion 304 and middle portion 303 and connecting web 103 extends completely around middle portion 303 and outer portion 302 when connecting flange 305 is secured to the syringe body 100, the needle cover 301 provides complete sterility for needle 310, FIG. 3, since it is both an air seal and a water seal. In certain applications in which a water seal is not required and it is desirable to reduce the breaking forces of the connecting webs 102 and 103, the connecting webs 102 and 103 can be segmented in such a manner that only portions of the webs or spokes hold the portions 302, 303 and 304 of the needle cover 301 together. Even with the connecting webs 102 and 103 segmented, sterility for the needle is maintained as will be described later. The needle 310 is held in a needle holder 311 which is crimped to the needle 310. The needle holder 311 provides proper holding force to retain the needle properly in the needle mounting structure. As shown in FIG. 3, the needle holder 311 has a hub 312 extending towards the outer portion of needle 310 and an expansion ring 313 extending towards the inner portion of needle 310. As shown in FIG. 1, fingers 104 are attached to the middle portion 303 of the needle cover 301. When the needle holder 311 is press fitted into the middle portion 303 of the needle cover 301, the expansion ring 313 engages the fingers 104 in such a manner that they deflect the fingers 104 in an outward direction so that their outer tips 105 engage surface 306 of inner portion 304 of needle cover 301. Surface 306 is provided with a step 106 which acts with outer tips 105 of fingers 104 to prevent outward movement of middle portion 303. Inserting the needle holder 311 into its correct assembled location deflects fingers 104 such that they are acting as a cantilever spring restrained by surface 306. Surface 306 is provided at its inner most end with another step 107 into which outer tips 105 engage as will be described later.

Since most disposable prefilled syringes require a plunger rod to move the plunger which transfers the fluid from the syringe chamber through the needle this disclosure shows the convenient method of assembling the plunger rod 320 over the needle assembly for storage and shipment. This overlapping of parts reduces the size of the packaging required during storage and shipment and also functions to maintain the sterility of the assembly if the connecting web 102 is segmented. Outer hub 312 of the needle holder 311 engages an inner recess 110 of outer portion 302 of needle cover 301 to form a path with two right angle bends between the needle 310 and connecting web 103. This non-direct line between the outer end of needle 310 and the outside of the unit as well as the covering provided by the plunger rod 320 to seal any openings in connecting webs 102 and 103 provide for sterility against airborne contaminants. As shown in FIG. 3, the plunger rod 320 is held onto the needle cover 301 by means of two projections 108 engaging an inside ring 120 on plunger rod 320. This interference between the projections 108 and the inside ring 120 prevent the plunger rod 320 from accidentally falling off the needle cover 301.

In order to activate the syringe, that is, moving the inner portion of the needle 310 into and through the closing diaphragm 401 of the syringe, a force must be applied to break the connecting web 102. This breaking force can be applied to the projections 321 of the plunger rod 320 in the direction towards the syringe body. Pressure on the projections 321 applies pressure to a shoulder 322 which in turn applies the same pressure to a mating shoulder 109 on needle cover 301. Since the connecting web 102 is designed so that the linear pressure on shoulder 109 breaks the connecting web 102, further pressure on the projections 321 will move the needle cover 301, the needle 310 towards the closing diaphragm 401 and continue until the needle 310 pierces the closing diaphragm 401. Guiding of the needle during movement of the needle 310 from the deactivated position to the activated position is done by surfaces that formed the connecting web 102 and the outer tips 105 of fingers 104 riding on surface 306. When the needle has completely pierced the closing diaphragm 401, the outer tips 105 latch into step 107 due to the spring force that was built into the fingers 104 when the needle holder 311 was inserted into the needle cover 301. When the outer tips 105 engage the step 107 the needle assembly cannot be withdrawn or retracted without distruction of parts. The activated needle assembly is shown in FIG. 4. After activation the inner end of needle 310 is inside the closing diaphragm 401 and therefore the needle remains sterile even if plunger rod 320 is removed from a needle cover 301.

In operation of syringes of this type, the syringe is first activated as just described. After activation the plunger rod is removed from the needle cover assembly and is assembled into the plunger at the other end of the syringe as previously described. Since the syringe may not be used at this time it is important that the injecting end of the needle remains sterile and protected. As a result, after activation and removal of the plunger rod the needle must still be protected by the outer portion 302. As was previously described, the outer portion 302 is held to the middle portion 303 by means of connecting web 103. Connecting web 103, as previously described, can be a complete enclosure around the body of the needle cover 301 or can be segments. In either case, airborne sterility is maintained, as previously described, by the mating of the outer hub 312 with inner recess 110. When the nurse or doctor wishes to utilize the syringe, the outer portion 302 of needle cover 301 is broken away from the needle assembly. This action can be done by pulling the outer cover 302 off thus breaking the web, or by turning the outer cover 302 thus breaking the web. The needle assembly is prevented from coming from the syringe in these motions due to the engagement of the outer tips 105 into step 107. In certain applications, as mentioned above, it may be desirable to break the connecting webs 102 and 103 by rotating the parts relative to one another. As a result, the needle assemblies can be made with projections, with flats, or other special configurations on the outside surface which would aid in hand rotation of the parts.

As a result of the above description when read in light of the accompanying drawings, it has been shown that a needle assembly can be manufactured with a minimum number of parts and that the needle cover is a single part. Even with these minimum number of parts the syringe can maintain its sterility during storage and/or shipment. It also has been shown that the syringe with the described needle assembly can maintain sterility even if submersed in a fluid.

The above description describes a system in which the needle cover is one molded part and is assembled to a cannula or needle by means of a needle holding member. Although the above description and drawings show a preferred embodiment of the invention, this invention should not be limited to the description and drawing but by the appended claims.

What is claimed is:

1. A unitized cover for a hypodermic syringe needle having an outer end, an inner end, and a middle section comprising; a first cover for said outer end, a second cover for said inner end, a third cover for said middle section, a first breakable means connecting said first cover and said third cover, a second breakable means connecting said second cover and said third cover, said first breakable means and said second breakable means connecting said first cover, said second cover, and said third cover to form a unitized structure.

2. A unitized cover for a hypodermic syringe needle according to claim 1, including mounting means for mounting said hypodermic needle to said third cover, deflectable means associated with said third cover such that said deflectable means are deflected by said mounting means.

3. A unitized cover for a hypodermic syringe needle according to claim 2, including retaining means associated with said second cover and said deflectable means to limit movement of said second cover with respect to said third cover when said second breakable means are broken.

4. A unitized cover for a hypodermic syringe needle according to claim 1, including mounting means for mounting said unitized cover to the hypodermic syringe.

5. A needle assembly attachable to a syringe body comprising a cannula having an outer section, an inner section, and a center section, a first cover member over said inner section of said cannula, attaching means for attaching said first cover member to said syringe body, a second cover member covering said middle section of said cannula and breakable means connecting said second cover member to said first cover member.

6. A needle assembly according to claim 5, including mounting means secured to said center section of said cannula for mounting said cannula to said second cover member.

7. A needle assembly according to claim 5, including deflectable members attached to said second cover member retaining means on said first cover member engageable with said deflectable members such that said second cover member can only move in one axial direction when said breakable means is broken.

8. A needle assembly according to claim 7, including a cannula mounting element, deflecting means on said cannula mounting element to deflect said deflectable members in spring pressure engagement with said first cover.

9. A needle assembly attachable to a syringe body comprising, a cannula having an outer section, an inner section and a center section, a first cover member covering said outer section, a second cover member covering said center section, and breakable means connecting said first cover member to said second cover member to form a unitized structure.

10. A needle assembly according to claim 9, including a cannula mounting member for mounting said cannula in said second cover member.

11. A needle assembly according to claim 10, including openings in said breakable means, a projection on said cannula mounting member, a cavity in said first cover member, said projection and said cavity forming a sterility barrier for said outer section of said cannula.

12. A needle assembly attachable to a syringe body comprising, a hollow cannula pointed at an outer end and an inner end, an assembled inactive position for said cannula, an operated active position for said cannula, a unitized cover for said hollow cannula, an outer section of said unitized cover, an inner section of said unitized cover and a center section of said unitized cover, a first breakable member between said inner cover and said center cover, a second breakable member between said outer cover and said center cover, said first breakable member breakable on movement of said cannula from said inactive position to said active position, said second breakable member breakable for exposing said outer end of said cannula.

13. A needle assembly attachable to a syringe body according to claim 12, including attaching means on said inner cover to attach said needle assembly to said syringe body.

14. A needle assembly attachable to a syringe body according to claim 13, including mounting means for said cannula, deflecting means on said center cover, said mounting means deflecting said deflecting means against said inner cover when said mounting means is assembled in said center cover.

15. A needle assembly according to claim 14, including restraining means on said inner cover and restraining elements on said deflecting means to restrict movement of said cannula for movement from said inactive position to said active position only.

* * * * *